(12) United States Patent
Vaes et al.

(10) Patent No.: US 8,816,685 B2
(45) Date of Patent: Aug. 26, 2014

(54) PULSED EPR DETECTION

(75) Inventors: Peter Vaes, Rijmenam (BE); Stephanie Teughels, Herent (BE)

(73) Assignees: IMEC, Leuven (BE); Pepric nv, Leuven (BE)

( * ) Notice: Subject to any disclaimer, the term of this patent is extended or adjusted under 35 U.S.C. 154(b) by 373 days.

(21) Appl. No.: 13/075,087

(22) Filed: Mar. 29, 2011

(65) Prior Publication Data

US 2012/0049847 A1 Mar. 1, 2012

Related U.S. Application Data

(63) Continuation of application No. PCT/EP2009/062723, filed on Sep. 30, 2009.

(60) Provisional application No. 61/225,424, filed on Jul. 14, 2009, provisional application No. 61/101,374, filed on Sep. 30, 2008.

(30) Foreign Application Priority Data

Apr. 17, 2009 (GB) .................................. 0906644.0
Jul. 10, 2009 (EP) ..................................... 09165120

(51) Int. Cl.
*G01V 3/00* (2006.01)
(52) U.S. Cl.
USPC ........................................... 324/316; 324/312
(58) Field of Classification Search
USPC .......................... 324/316, 312, 314, 307, 300
See application file for complete search history.

(56) References Cited

U.S. PATENT DOCUMENTS

| 4,940,966 | A | 7/1990 | Pettigrew et al. |
| 5,502,386 | A * | 3/1996 | Bourg et al. .................. 324/316 |
| 6,924,150 | B1 | 8/2005 | Xiang et al. |
| 8,283,926 | B2 * | 10/2012 | Teughels et al. .............. 324/316 |
| 2004/0026028 | A1 | 2/2004 | Kirsten et al. |
| 2004/0138554 | A1 | 7/2004 | Dimmer et al. |
| 2005/0118102 | A1 | 6/2005 | Xiang et al. |
| 2005/0179552 | A1 | 8/2005 | Shoji et al. |

FOREIGN PATENT DOCUMENTS

WO   WO 97/04331   2/1997

OTHER PUBLICATIONS

Eaton et al., Spin Lattice Relaxation—Part 1, Solids, Department of Chemistry and Biochemistry, University of Denver, Presented at Retie, Belgium, Dec. 1-7, 2002.

Hubrich et al., Pulse-Train-Detected Electron-Spin-Echo Envelope Modulation, Journal of Magnetic Resonance, Series A, vol. 114, No. 2, 1995, pp. 271-273.

Moreland et al., Ferromagnetic Resonance Spectroscopy with a Micromechanical Calorimeter Sensor, Review of Scientific Instruments, vol. 71, No. 8, Aug. 2000, pp. 3099-3103.

Poole et al., Electron Spin Resonance—A Comprehensive Treatise on Experimental Techniques, 1983, pp. 618-627, John Wiley & Sons, New York.

(Continued)

*Primary Examiner* — Louis Arana

(74) *Attorney, Agent, or Firm* — Knobbe Martens Olson & Bear LLP

(57) ABSTRACT

A method and system for performing pulsed electron paramagnetic resonance is disclosed. In one aspect, the method includes generating an excitation pulse train for applying to an object having probes and detecting from the probes an echo response induced by the excitation pulse train.

19 Claims, 7 Drawing Sheets

(56) References Cited

OTHER PUBLICATIONS

Schweiger et al., Coherent and Incoherent Echo Spectroscopy with Extended-Time Excitation, Physical Review Letters, vol. 54, No. 12, Mar. 25, 1985, pp. 1241-1244.

Schweiger et al., Principles of Pulse Electron Paramagnetic Resonance, Dec. 15, 2001, pp. 192-197, 1st Edition, Oxford University Press, USA.

Shellock et al., Magnetic Resonance Procedures: Health Effects and Safety, Dec. 21, 2000, pp. 425-443, 1st Edition, CRC Press LLC, Boca Raton, Florida.

European Search Report mailed Dec. 17, 2009 in European Application No. 09165120.8.

International Search Report and Written Opinion mailed Jan. 25, 2010 in International Application No. PCT/EP2009/062723.

International Preliminary Report on Patentability mailed on Aug. 27, 2010 in International Application No. PCT/EP2009/062723.

* cited by examiner

PULSED EPR DETECTION

CROSS REFERENCE TO RELATED APPLICATIONS

This application is a continuation of PCT Application No. PCT/EP2009/062723, filed Sep. 30, 2009, which claims priority under 35 U.S.C. §119(e) to U.S. provisional patent application 61/101,374 filed on Sep. 30, 2008 and to U.S. provisional patent application 61/225,424 filed on Jul. 14, 2009. Each of the above applications is incorporated herein by reference in its entirety.

BACKGROUND OF THE INVENTION

1. Field of the Invention

The disclosed technology relates to the field of electron paramagnetic resonance. More particularly, the technology relates to methods and systems for applying pulsed electron paramagnetic resonance.

2. Description of the Related Technology

Magnetic resonance techniques are widely spread and find their application in amongst others detection and imaging. Whereas continuous working often may be inefficient as during a magnetic field scan most of the time baseline data is recorded between resonance responses, pulsed magnetic resonance typically uses the measurement time to a better effect. In pulsed magnetic resonance an impulse excitation is applied at the resonant frequency and the Fourier transform of the resulting free induction decay signal reveals the spectrum. The pulsed magnetic resonance technique may result in sensitivity advantages. In pulsed electro paramagnetic resonance (EPR) measurements, a short pulse is applied on a probe after which the magnetization of the probe is measured.

One problem with pulsed EPR is that the ring-down of the antenna caused by de-phasing of the spins, lasts longer than the free induction decay (FID), i.e. the signal to be detected, coming from the probe. This FID is longer when the line width of the probe is smaller. It consequently has been found previously that pulsed EPR should be limited to probes with a line width smaller than 3 MHz or that for pulsed EPR it is desirable to have spin probes, which have a very narrow single line spectrum because the transverse relaxation time is inversely proportional to line width. The problem of pulsed EPR for probes with a broad line width is shown in FIG. 1. FIG. 1 illustrates the initial alignment of spins with a static magnetic field along the Z-axis (part (a)), the subsequent alignment of the spins along the Y-axis after a Π/2 pulse, which would allow capturing of the probe signal by the antennas (part (b)), and the de-phasing of the spins resulting in the probe signal being not available (part (c)).

Some solutions have been provided to measure a short probe signal without being influenced by the ring-down time of the antennas. One known technique is the use of the Hahn echo. Using the Hahn echo, a first pulse will flip the spins 90 degrees with respect to the static magnetic field. During a period of time the tilted spins will de-phase (each with its own frequency), after which a second pulse will tilt the spins 180 degrees. Due to this pulse, the spins will re-phase. They will be re-phased exactly after a time equal to the time between the pulses. At this moment the echo can be measured.

It is also known to use pulse trains as a preparation technique for experiments. Some techniques are known for obtaining material characteristics wherein a set of three pulses is first used for creating a stimulated echo, and whereby a response of the material is induced by a re-phasing pulse. Other techniques use variations of applying pulses or pulse trains, but these all use a re-phasing pulse to induce a response of the material.

It is known to use shaped sinc pulses to achieve a more uniform power excitation over a relatively wide bandwidth region. For example, a truncated sinc pulse may be used to compensate for the Q-profile of the antenna.

It is also known, for techniques applying a pulse sequence, to correlate the input sequence with the measured result. One way to perform this is to change the phase between the pulses to eliminate the overlap of signals after multiple pulse sequences. Another example is correlating FID with the input sequence, to decrease the total acquisition time and to improve the signal to noise ratio of the FID signal.

SUMMARY OF CERTAIN INVENTIVE ASPECTS

Certain inventive aspects relate to methods and system applying pulsed electron paramagnetic resonance (EPR). It is an advantage of certain embodiments that methods and systems are obtained allowing pulsed EPR detection on probes with broad line widths. It is an advantage of certain embodiments that methods and systems are provided that can be used with super-paramagnetic nano-particles and that allow full exploitation of the wide resonance of such super-paramagnetic nano-particles.

It is an advantage of certain embodiments that the power may be distributed over the sequence of pulses allowing tilting the spins gradually during each pulse and allowing a large overall power being applied for detection.

It is an advantage of certain embodiments the power for individual frequencies can be adapted to the antenna system and/or to the resonance of the probes.

It is an advantage of certain embodiments that a pulse sequence is used to selectively excite certain frequencies of the broadband probes, in order to create an echo sequence coming from the probes. The echo sequence coming from the probes thereby is based on positive interference.

It is an advantage of certain embodiments that pulsed EPR methods and systems are provided allowing imaging of objects. It is an advantage of certain embodiments that a good imaging technique, e.g. in-vivo imaging technique, can be obtained. The latter can be obtained by generating an echo using a pulse train and using the echo for imaging.

It is an advantage of certain embodiments, over known systems using a sequence of pulses, that it exploits positive interference of the spins for detecting or imaging. The positive interference can be induced to occur on a periodic basis.

It is an advantage of certain embodiments that only a limited number of frequencies of the wideband resonance can be activated.

It is an advantage of certain embodiments that methods and systems are provided using pulse trains in order to generate an echo for imaging.

One inventive aspect relates to a method for performing pulsed electron paramagnetic resonance, the method comprising generating an excitation pulse train for applying to an object comprising probes, and detecting from the probes an echo response induced by the excitation pulse train. It is an advantage of certain embodiments that there is no need for a rephasing pulse, but that the response may be directly induced by the pulse train.

Generating an excitation pulse may comprise generating an excitation pulse inducing positive interference effects between responses of the probes for forming the echo response.

Detecting an echo response may comprise topologically imaging echo responses from probes distributed in the object.

Generating an excitation pulse may comprise selectively exciting predetermined frequencies of broadband probes of interest.

Detecting an echo response may comprise detecting an echo response from single domain particles.

Detecting an echo response may comprise detecting an echo response from wideband resonance super paramagnetic particles. The resonance response of the probe may occur in a wide band, e.g. between about 3 MHz and 400 MHz. The wideband signal coming from the transmitter may be considered wideband if the frequency range in which the response occurs is larger than about 20% of the central frequency, which may vary between about 60 MHz and 500 MHz.

Generating an excitation pulse train may comprise generating a sequence of EPR pulses wherein the shape of the different EPR pulses is adapted for compensating at least partly for frequency dependency of the resonance of spin probes in the object.

It is an advantage of certain embodiments that compensation for frequency dependency of resonance of spin probes can be obtained as such frequency dependency becomes especially relevant for probes with large linewidths.

Generating an excitation pulse train may comprise generating a sequence of EPR pulses, whereby the intensity of the different EPR frequencies is adapted for compensating at least partly for power dependency of the resonance of spin probes in the object or of a detection system.

The method also may comprise generating a static magnetic field for applying to the object comprising spins for providing an initial alignment of the spins, wherein generating an excitation pulse train comprises generating pulses having a substantially different orientation than the static magnetic field.

One inventive aspect relates to a system for performing pulsed electron paramagnetic resonance, the system comprising an excitation pulse train generator for generating an excitation pulse train for applying to an object comprising probes, and a detection unit for detecting from the probes an echo response induced by the excitation pulse train.

The excitation pulse train generator may comprise a controller for selectively exciting predetermined frequencies of broadband probes of interest and for generating an excitation pulse train positive interference effects between responses of probes for forming the echo response.

The detection unit may be adapted for topologically imaging echo responses from probes distributed in the object.

One inventive aspect relates to a method for preparing pulsed electron paramagnetic resonance measurements, wherein the method comprises designing an excitation pulse train adapted for inducing an echo response from probes, e.g. probes having a wide linewidth, based on positive interference between the individual responses of the probes to the individual frequencies of the excitation pulse train.

One inventive aspect relates to a computer program product for, when executed on a computing device, performing a method as described above. Furthermore, a data carrier comprising a computer program product as described above and/or transmission of such a computer program product over a network is also envisaged.

Certain inventive aspects are set out in the accompanying independent and dependent claims. Features from the dependent claims may be combined with features of the independent claims and with features of other dependent claims as appropriate and not merely as explicitly set out in the claims.

Certain embodiments will now further be discussed in the detailed description in conjunction with the drawings. The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF CERTAIN ILLUSTRATIVE EMBODIMENTS

Figure 1:
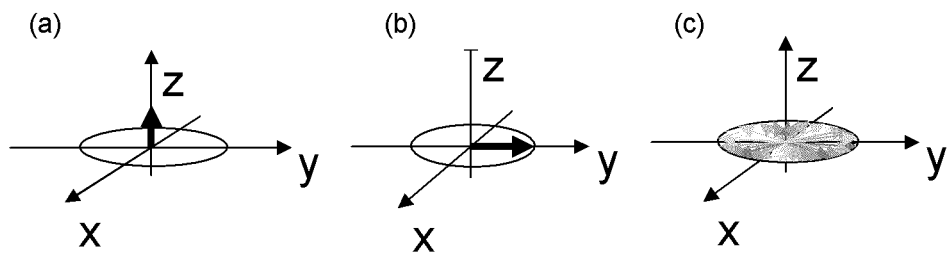
FIG. 1 illustrates the problem of de-phasing of spins and its effect on the probe signals to be detected, as known from prior art.

In the following detailed description, numerous specific details are set forth in order to provide a thorough understanding of the disclosure and how it may be practiced in particular embodiments. However it will be understood that the present disclosure may be practiced without these specific details. In other instances, well-known methods, procedures and techniques have not been described in detail, so as not to obscure the present disclosure. While the present disclosure will be described with respect to particular embodiments and with reference to certain drawings, the reference is not limited hereto.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the steps or elements listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B. Where reference is made to the term consists of the latter implies that no other elements are present.

Where in embodiments of the present application the term nano-particles is used, reference is made to particles having a critical dimension, e.g. diameter, in the range of about 1 nm to 1000 nm. Certain embodiments make use of the magnetization of single domain particles. Single domain particles are defined as particles having a maximum coercivity for a given material occurring within its single domain range. Having larger grain sizes, coercivity decreases as the grain subdivides into domains. For smaller grain sizes, coercivity again decreases, but this time due to the randomizing effects of thermal energy. The critical size for single domain behavior depends on several factors including, the saturation magnetization and the shape of the grain. In single domain particles, the local magnetization is saturated but not necessarily parallel. Domains are larger than atomic distances and typically between about 1 and 100 nanometer.

Super-paramagnetic particles are a specific class of single domain particles. As the particle size continues to decrease within the single domain range, the remanence and coercivity go to zero. When this happens, the grain becomes super-paramagnetic.

A single particle of volume v has a uniform magnetization directed along the easy axis of magnetization. If v is small enough, or the temperature is high enough, thermal energy (kT) will be sufficient to overcome the anisotropy energy separating the (+) and (−) magnetization states and cause a spontaneous reversal of magnetization The measured signal of such single domain resonant particles is proportional to the magnetization. Therefore, it is beneficial to use particles made of a compound that show an electron paramagnetic resonance (EPR) with a magnetization being lower than the saturation magnetization.

Where in the present text reference is made to a broad line width, reference may be made to a line width of about 3 MHz or larger, e.g. in a range from about 3 MHz to 400 MHz.

It is an advantage of certain embodiments that pulsed electron paramagnetic resonance methods and systems can be obtained providing good operation with probes having a broad line width, e.g. a line width of about 3 MHz or larger.

Figure 2:
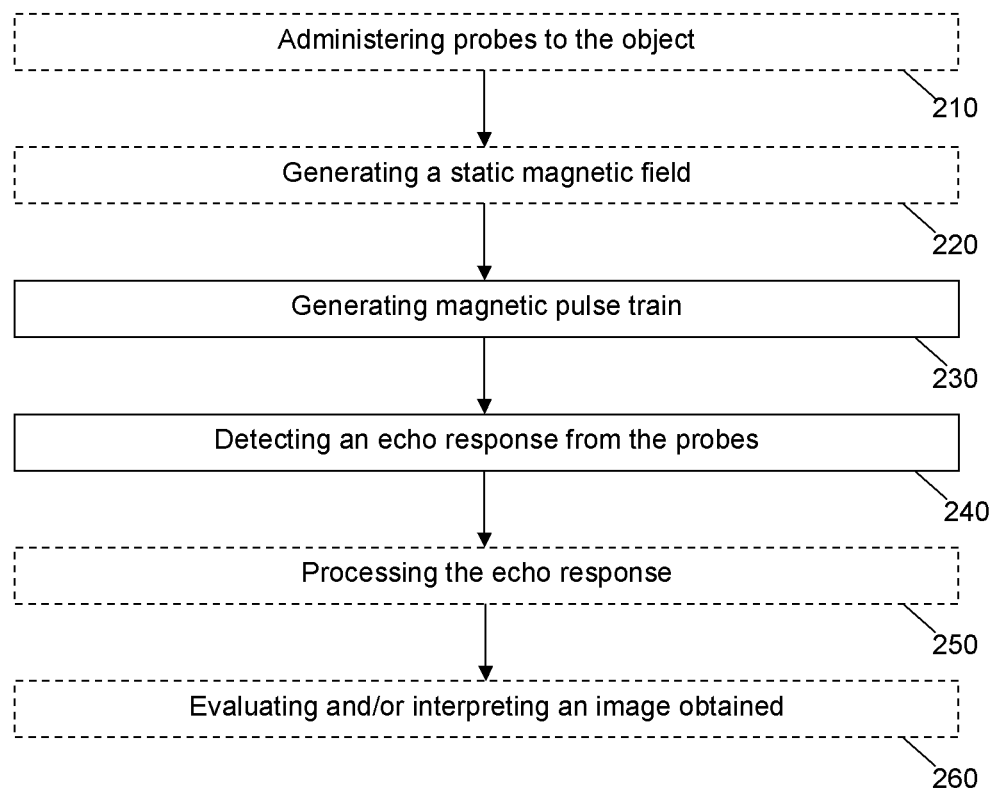
FIG. 2 illustrates a flow chart of a method for performing pulsed electron paramagnetic resonance according to one embodiment.

In a first aspect, there are a method and system for performing pulsed electron paramagnetic resonance (EPR). Certain embodiments may be especially suitable for imaging purposes, even when probes are used with broad line width. Certain embodiments may be especially suitable for exploiting the wide resonances of single domain particles, e.g. of super-paramagnetic particles, e.g. super-paramagnetic nano-particles. The method for performing pulsed EPR comprises generating a train of pulses for applying to an object comprising probes and detecting an echo response induced by the train of pulses from the object comprising probes. The actual process of applying the train of pulses to the object, e.g. by directing the pulses, in that direction may or may not be part of the method. By way of illustration, the present disclosure not being limited thereto, the different standard and optional processes will be described in more detail, with reference to a flow chart of an exemplary method according to one embodiment, as shown in FIG. 2.

In a first optional process 210, which may be an external process not part of the method for performing pulsed EPR on an object, administering of probes to the object may be performed. The latter may be performed using conventional techniques, such as for example, administering via a contrast liquid. The probes used for detecting and/or imaging may be single domain particles, such as for example super-paramagnetic particles as described above, although the disclosure is not limited thereto. In advantageous embodiments, the probes are administered intravenously. Such probes can be coated with different types of molecules depending on the target they should reach. One example thereof is coating with Dextran which will allow targeting the liver, but it is clear to the person skilled in the art that each suitable particle targeting the target of interest could be used. Selection may be based on the application envisaged. One example of a contrast agent that could be used is resovist. This contrast agent may for example comprise a concentration of about 0.5 mmol Fe/ml.

For measurements, the method typically may comprise generating a static magnetic field, indicated as process 220. The generated static magnetic field may be generated by a static magnetic field generator or generating unit for example using a permanent magnet, an electromagnet, etc. The generated static magnetic field may be for applying such a static magnetic field to an object, so that probes in an object can be oriented along the direction of the static magnetic field. By way of illustration, the present disclosure not being limited thereto, in the following description it is assumed that the static magnetic field results in an initial orientation of the probes along the Z-direction. A typical magnitude of the applied static magnetic field may for example be in the range having a lower limit of about 1 Gauss and an upper limit of about 300 Gauss. Moreover an additional field gradient can be applied. This means the static field will be different for different positions and this will allow obtaining a spatial resolution between the probes.

The method furthermore comprises generating 230 a train of excitation magnetic pulses for directing them towards the object comprising probes. The excitation magnetic pulses may be induced using a magnetic pulse generator or generating unit, such as for example an electromagnet, a moving permanent magnet, etc. The pulses may, in some embodiments, be amplified and transmitted afterwards using an antenna, such as for example a coil antenna. The excitation pulse train thereby may comprise more than 2 pulses, advantageously more than 3 pulses. The total number of pulses advantageously depends on the power required for tilting the spins. As such it depends on the power available in one pulse, and on the probe itself. The pulses are oriented in the X-Y plane (original orientation of the spins is along the Z-axis). The important component of these pulses is rotating in the X-Y plane with a frequency corresponding with the Larmor frequency of the probe. It is this component that will tilt the electron-spin. The pulse height of the different excitation pulses may be in a range having a lower limit of about 1 mW and an upper limit of about 10 MW. The pulse shape used may be any suitable pulse shape, such as for example a sinc pulse or a modified sinc pulse. Other examples are block pulses or any other form created by summing the individual frequencies which are the most appropriate for generating the echo signal from the probe. Generating such a pulse train may be realized by summing a set of individual frequencies. The pulse train may be generated such that selectively certain frequencies of the probes, e.g. broadband probes are excited, so that an echo response is induced. The pulse train in the time domain may correspond with a frequency grating in the frequency domain. The distance between the pulses may be inversely proportional to the spacing between the frequencies. A typical length of the pulse train may be in a range having a lower limit of about 10 ns and an upper limit of about 1 ms.

The method also comprises detecting 240 a response from the probes. Such a response may be detected using a detection unit or detector, e.g. a receiving antenna. The probe spins in the object will transmit, as response to the pulse train generated, a pulse train having similar characteristics afterwards. More particularly, a pulse train with the same frequencies and with the same phase relations may be detected by a detection unit, e.g. a receiving antenna. The width in the frequency domain thereby will be inversely proportional to the pulse width of the pulses in the pulse train. As the response pulse train has the same frequencies and the same phase relations, it is referred to as an echo response. The response may be induced by positive interference between the individual exited frequencies. The response will be built up as from application of the exciting pulse train and will be continued after the exciting pulse train has finished.

The time between the last stimulus pulse and the echo signal (is inversely proportional to the frequency step. This time should be bigger than the dead-time of the receiving system to enable the detection of the echo signal. Since particles with broad line widths are used, this principle allows having an echo signal after the dead time of the receiver, and before the relaxation time of the particles.

Upon or after detection of the echo response, the method furthermore optionally may comprise processing 250 the echo response for deriving properties of the probes. Such properties may for example be presence of the probes, number of the probes present, etc. In an advantageous embodiment, detection of the echo response can be performed as function of the position of the probes, allowing generating an image of the probes. In other words the echo response may be recorded in a topologically consistent manner, allowing to make an image of the distribution of the probes in the object. Such detection may for example be performed by scanning the object with the receiving antenna. Alternatively or in addition thereto, a static magnetic field with a field gradient may be used. By applying a field gradient of the static magnetic field, and this in the different directions, the probes will have a different frequency response depending on their position. Moreover multiple antennas can be used, the position of the antennas can be changed and the orientation of the magnetic field gradient can be changed. These latter solutions provide the advantage of resulting in a fast imaging technique.

A further optional process, which may be part of the method or which may explicitly not be part of the method, may comprise evaluation and/or interpreting 260 an image obtained. The latter may for example be performed to derive a status of an object, monitor an evolution of an object, etc.

Figure 3:
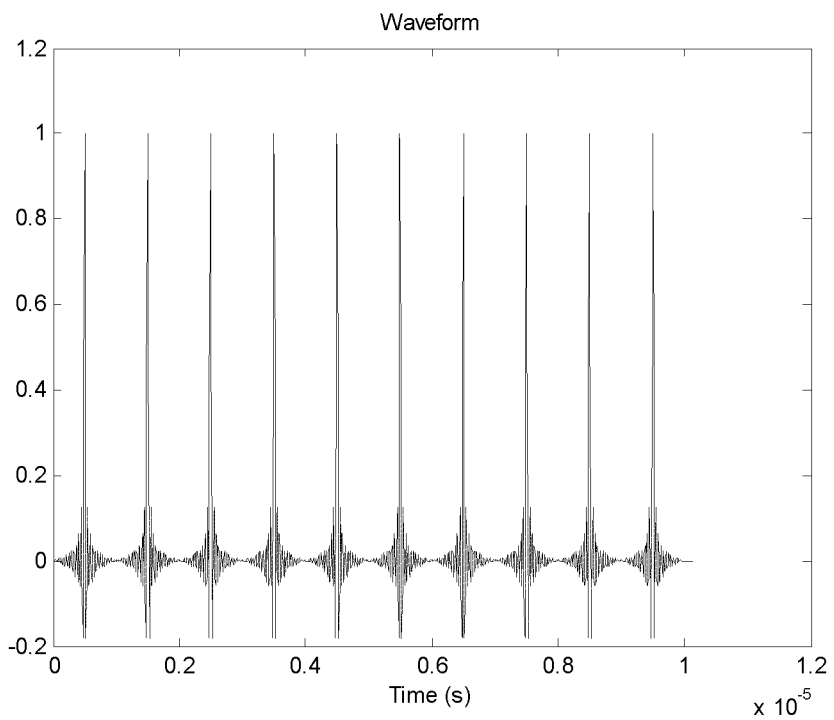
FIG. 3 illustrates an example of an excitation pulse train as can be used in a method for performing pulsed electron paramagnetic resonance according to one embodiment.
Figure 4:
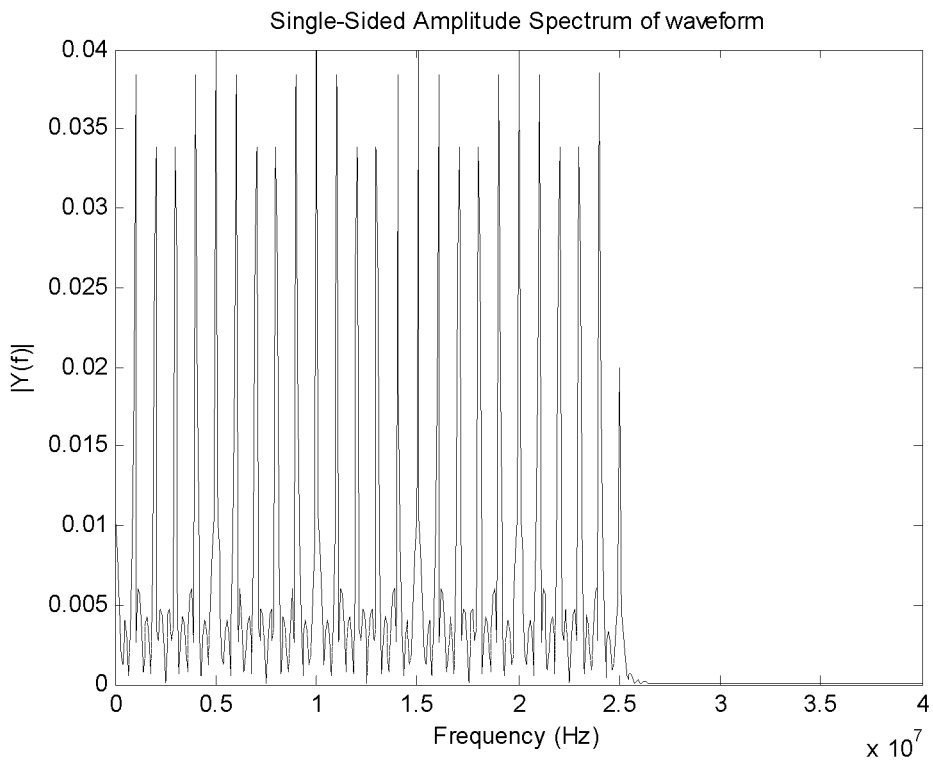
FIG. 4 shows the Fourier Transform of the excitation pulse train shown in FIG. 3.

By way of illustration, the present disclosure not being limited thereto, an example of the pulse trains applied and obtained when performing an exemplary method according to one embodiment are further discussed. By way of illustration, FIG. 3 shows a pulse train as can be generated and FIG. 4 illustrates a Fourier transform thereof. In the present example, the pulse train has a total bandwidth of 50 MHz and the spacing between the frequencies is 1 MHz. This results in spacing between the pulses of 1 µs.

Figure 5:
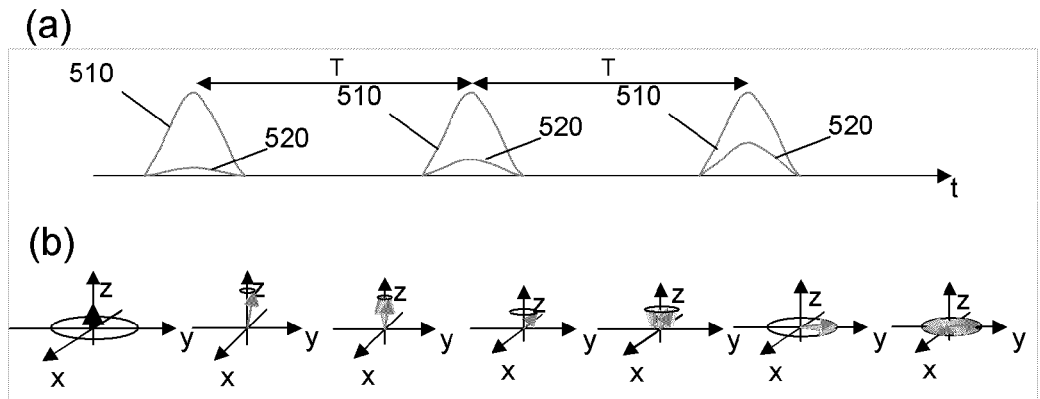
FIG. 5 and FIG. 6 illustrate an excitation pulse and the corresponding probe echo response both in amplitude and in resulting orientation.
Figure 6:
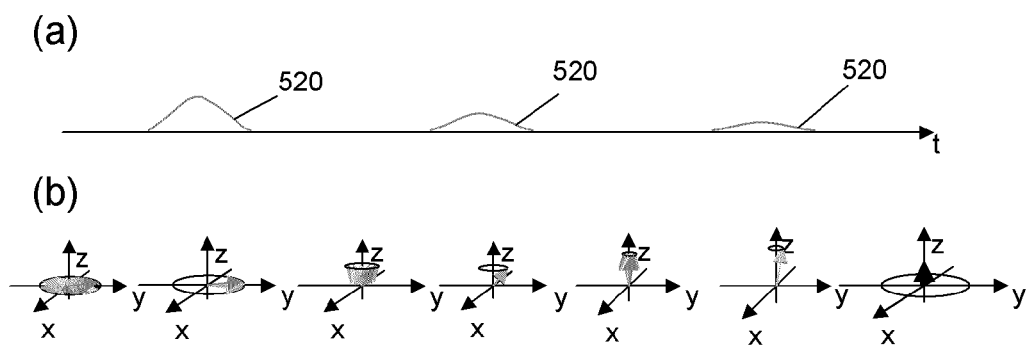

In FIG. 5, an example of an applied pulse train and the initial response of the probes is shown by way of illustration, the present disclosure not being limited thereto. In FIG. 5 part (a), pulses 510 are the pulses generated for applying to the object, whereas pulses 520 are the echo responses from the probes. It is to be noticed that the figure is illustrative and scales are not matching with reality. As indicated above, the distance between the pulses is the inverse of the frequency spacing. In FIG. 5 part (b), the initial response of the probes can be seen. The variation of the probe response in time is shown from left to right. In the drawing at the left, the initial orientation of the static magnetic field is shown, being the direction along which the probes will be oriented. It can be seen that initially in the present example, the probes are oriented along the Z-direction, i.e. the orientation provided by the static magnetic field. The next drawings each time illustrates the resulting magnetic moment of the electron spin. As reply to the pulses induced, the probes start to tilt towards the x-y plane. Between the pulses, the spins will de-phase since different frequencies are excited. After each pulse the spins will be tilted more towards the x-y plane and rephase. This means also that after each pulse the spins will generate a bigger signal. The pulse train is continued until the spins are tilted 90 degrees. Additionally the spins will try to align themselves with the static magnetic field along the Z-axis. When no further pulses are applied, the spins will align with the z-axis and upon alignment, the signal from the spins will be reduced to zero. After the initially applied pulse train has ended, the further resulting response signal coming from the probes is shown in FIG. 6. Again the overall reply is shown by pulses 520 in part (a), whereas the corresponding particular probe orientation is shown in part (b) indicating the spin magnetic moment and its de-phasing and re-phasing. As can be seen the reply of the probes is a pulse train having similar frequency and phase as the initially applied pulse train, and therefore can be referred to as an echo response.

In one embodiment, the characteristics of the excitation pulse train are selected so as to improve or optimize the signal to noise ratio. By increasing the step size between the frequencies the pulse repetition rate can be made faster. This allows putting more power during a shorter period of time into the system. However when increasing the frequency steps, less probes will be activated. The signal to noise ratio can be improved or optimized by choosing a good, improved or optimal step size taken into account the relaxation times of the probes. By way of illustration, for one example the frequency steps, also referred to as frequency grating, can be selected such that the first echo after the pulse train occurs just after the end of the ring-down of the antennas. The ring-down is selected smaller than the time for alignment with the Z-axis. After ring down and before alignment, an optimum signal to noise ratio can be obtained.

Figure 7:
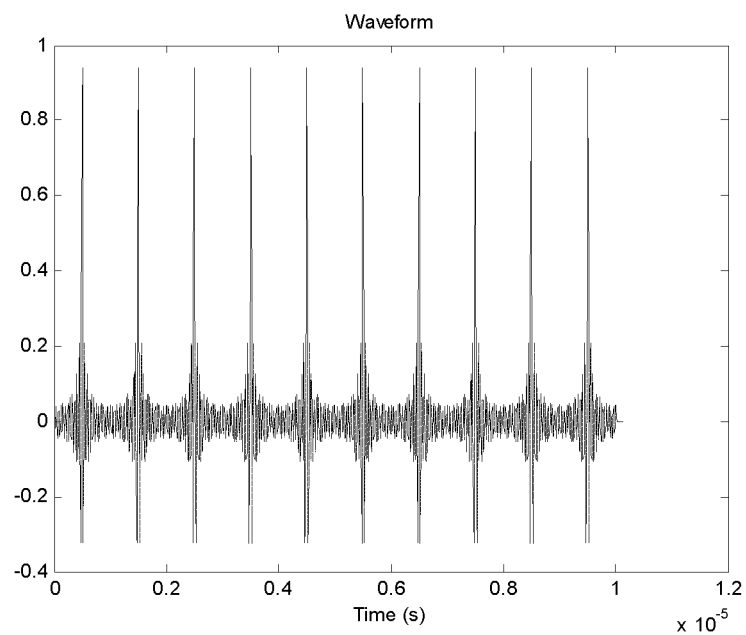
FIG. 7 illustrates an example of an excitation pulse train adapted to provide different power for different frequencies, as can be used in certain embodiments.
Figure 8:
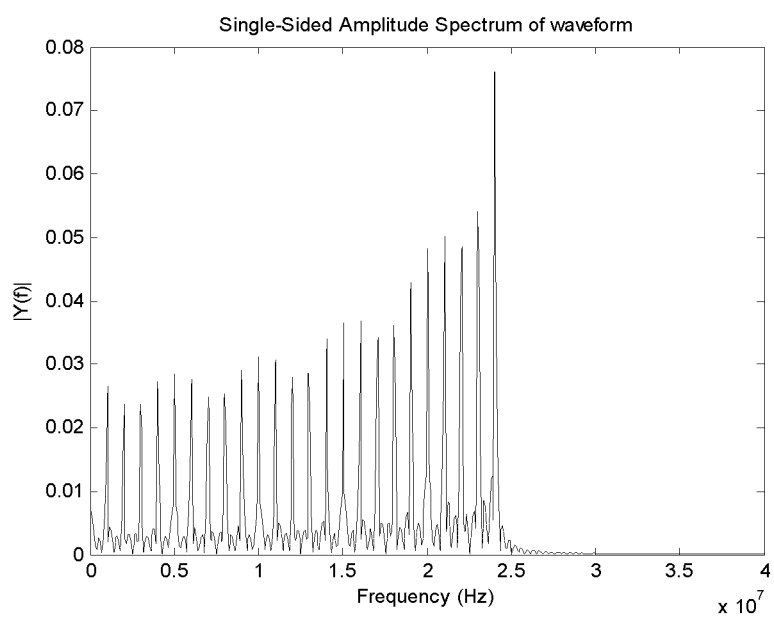
FIG. 8 illustrates a Fourier transform of the excitation pulse train shown in FIG. 7.

In one embodiment, the shape of the pulses in the pulse train may be adapted in order to improve or optimize the response of the probes. The latter may be particularly suitable for probes having a broad line width. By shaping the pulses, the amplitude and/or phase of each of the individual frequencies excited by the excitation pulse can be modified such that each of the probes, e.g. spins, can generate a good, improved or maximum signal. In one embodiment, the amplitude, corresponding with the excitation power provided, for a plurality of or for each of the composing frequencies can be separately modified to match with the individual probes. By way of illustration, FIG. 7 and FIG. 8 illustrate an excitation pulse train and its Fourier Transform for the situation whereby at lower frequencies less power is required to induce a probe spin flip of 90 degrees and at higher frequencies more power is required. It can be seen that by tuning the shape of the pulses in time domain, the corresponding frequency domain excitation provides the appropriate excitation power. In one embodiment, the excitation pulse train may, alternatively or in addition thereto, also be adapted to compensate effects induced by the transfer function of the antenna used for detecting the echo reply.

In one embodiment, optimization can be done by choosing the optimal bandwidth of the pulse train, depending on the line width of the probes to be measured.

One embodiment relates to a method and system as described above, wherein furthermore the excitation pulse train is adapted for exploiting correlation between the excitation pulses and the echo response. The number of frequencies, the spacing between the frequencies, the amplitude and the phase of each of the frequencies may be particularly tuned. As the signature of the excitation pulses in the pulse train and the echo pulses in the echo response are the same, the signal to noise ratio can be increased using spread spectrum techniques. Therefore pulses with different shapes may be used. Any of the frequencies can have a specific amplitude/phase. In one example, the resulting transmit sequence can be applied to the probes. When correlating the transmitted signal with the received signal coming from the probes, the resulting signal will be maximum for those probes which are excited with the corresponding pulse train. In a multiple antenna setup this could be used to distinguish between the different antennas. Different pulse shapes also can be used to obtain a better space resolution.

Figure 9:
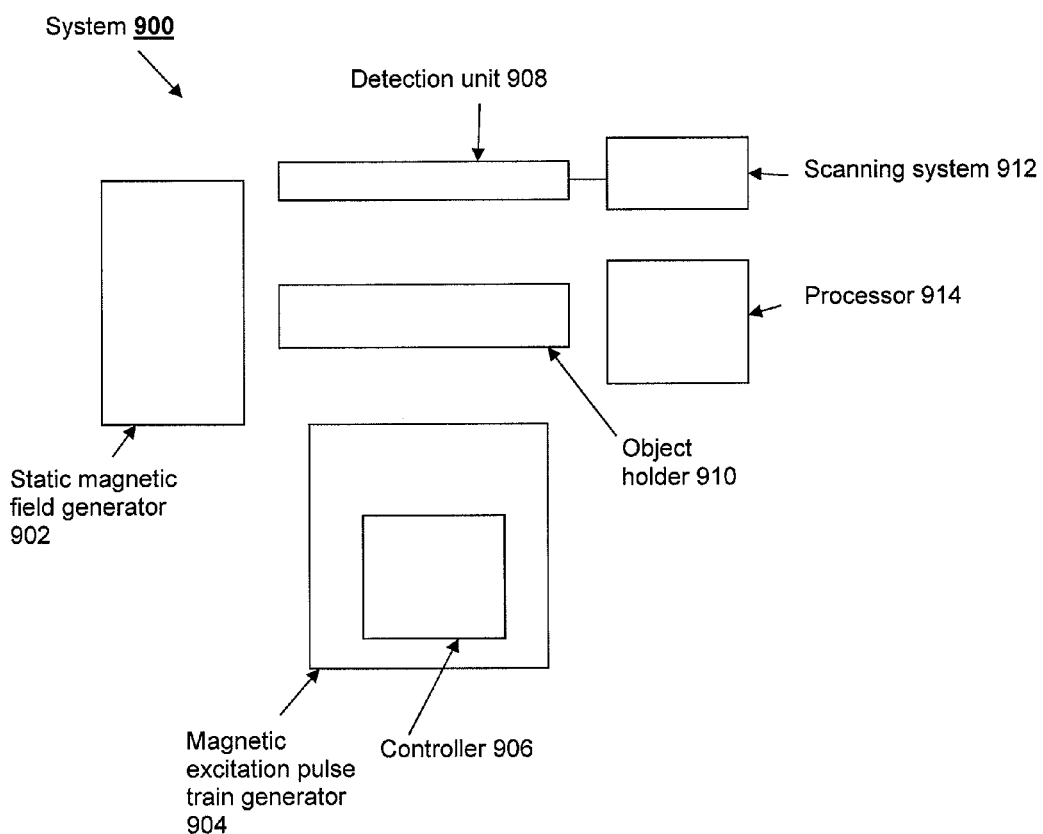
FIG. 9 illustrates a system for performing pulsed electron paramagnetic resonance according to one embodiment.

Certain embodiments relate to a system for performing pulsed electron paramagnetic resonance. Such a system advantageously may be adapted for performing a method as described in more detail above. The system 900, an example according to one embodiment being shown in FIG. 9, typically comprises a static magnetic field generator 902. Such a static magnetic field generator or generating unit 902 may be any type of magnetic field generator such as for example a permanent magnet, an electromagnet. The system 900 comprises a magnetic excitation pulse train generator or generating unit 904, adapted for generating an magnetic excitation pulse train. Such a magnetic excitation pulse train generator 904 may be of any suitable means, such as for example an electromagnet antenna. The magnetic excitation pulse train generator 904 may be adapted for generating an excitation pulse train so that an echo response is generated by the probes based on positive interference between the responses. The magnetic excitation pulse train generator 904 may comprise a controller 906 adapted for controlling the magnetic excitation pulse train generator 904 accordingly. Such a controller 906 may for example be implemented as software run on a processor or as hardware. Alternatively, the controller may be a separate component co-operating with the magnetic excitation pulse train generator 904. The system 900 furthermore comprises a detection unit or detector 908, adapted for detecting an echo response from the object under study. Such a detector 908 may be a receiving antenna. The system furthermore may comprise one or more of an object holder 910, such as for example an object table, a scanning system 912 for detecting information in a topological manner, a processor 914 for processing the results obtained with the detector 908 the obtained results, etc. Other features may be as known in known pulsed electron paramagnetic resonance systems or may be features expressing functionality as described above for the pulsed EPR method.

In a second aspect, there is a method for preparing pulsed electron paramagnetic resonance measurements. The method comprises designing an excitation pulse train adapted for inducing an echo response from probes, e.g. probes having a wide linewidth, based on positive interference between the individual frequencies that are excited by the excitation pulse train Designing thereby may take into account adjusting or selecting the characteristics of the excitation pulse train to improve or optimize signal to noise ratio, for example by selecting an appropriate step size between the frequencies used for the excitation pulse train. Designing, in addition or alternatively also may comprise adjusting or selecting a particular pulse shape, for example selecting an appropriate amplitude or phase for one, more or each of the frequencies used in the excitation pulse train. Designing may, in addition or alternatively thereto, comprise selecting an optimal bandwidth, depending on the line width of the probes to be measured. As indicated above, in one example the frequencies could be selected such that the first echo signal after the pulse train is just after the end of the ring-down of the antennas, resulting in an optimum signal that can be measured.

By way of illustration, embodiments of the present disclosure not being limited thereby, an exemplary experiment is discussed illustrating the effect of a pulse train on the EPR response received. It can be seen that a response is obtained which is an effect of the pulse train and which does not occur for single pulses.

Figure 10:
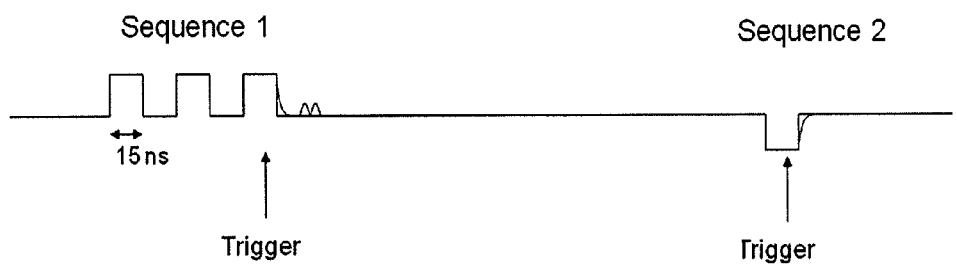
FIG. 10 illustrates an example of a combination of sequences as used in an exemplary EPR detection experiment using pulse trains.
Figure 11A:
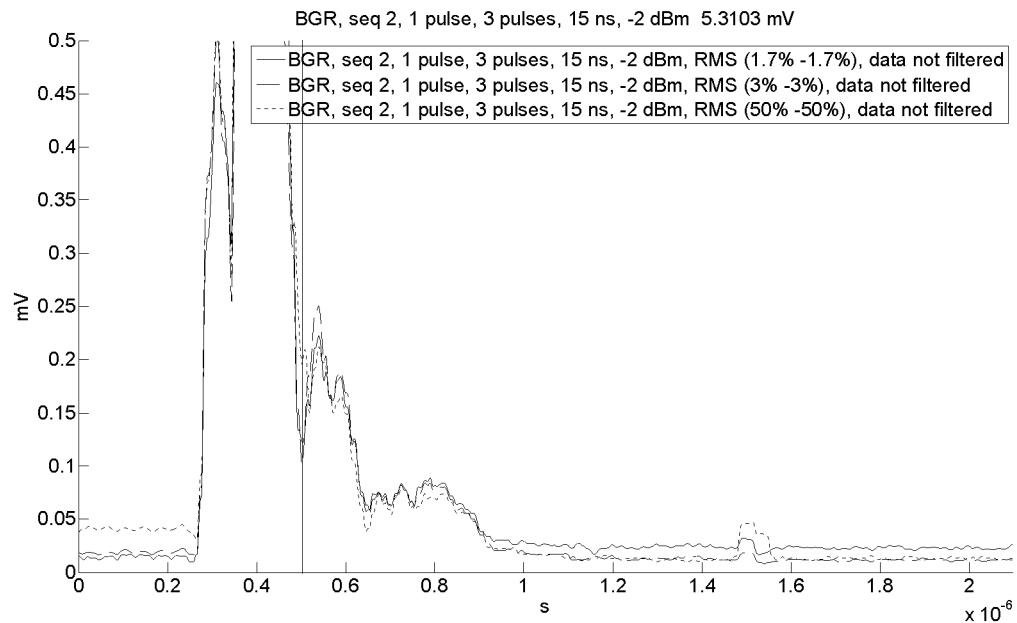
FIG. 11a to FIG. 11c illustrates the effect of the a combination of pulse sequences as shown in FIG. 10 on the EPR detection for the background FIG. 11a, on resovist in FIG. 11b and on 25 nm superparamagnetic particles in FIG. 11c.
Figure 11B:
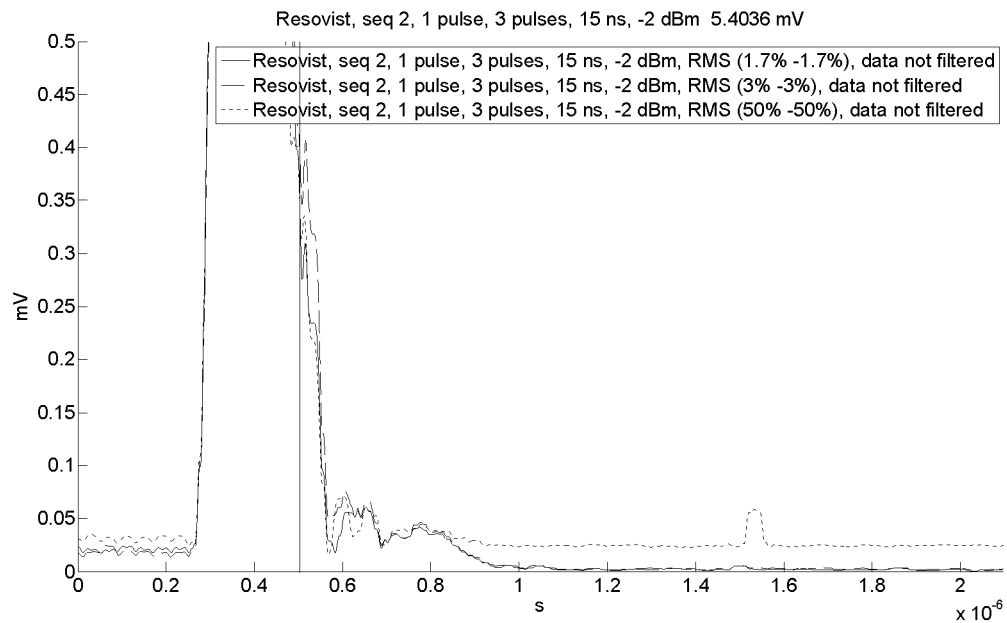
Figure 11C:
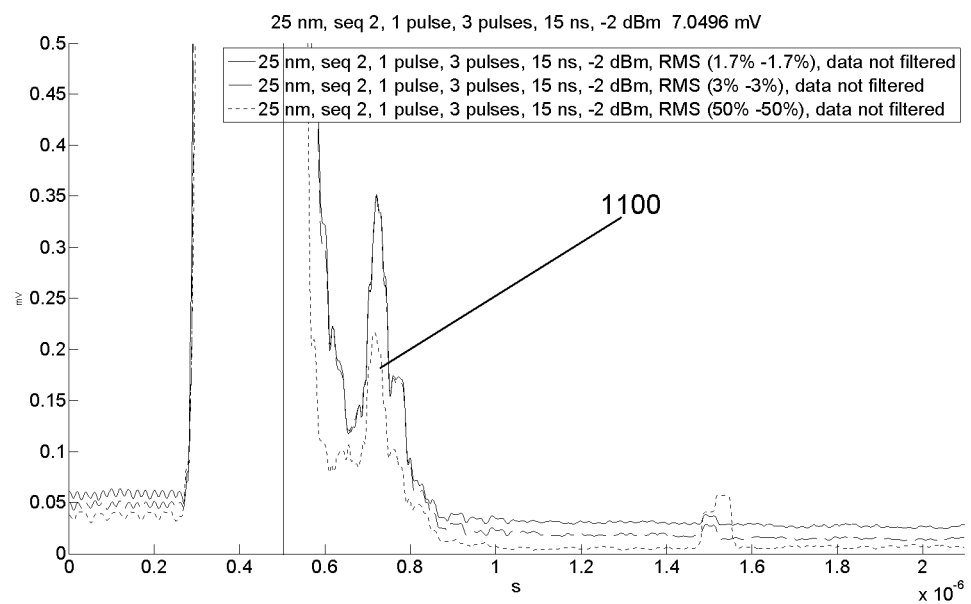

In the experiment, the effect of a pulse train on resovist particles and on super paramagnetic particles with a diameter of 25 nm is evaluated. The experiment is performed by applying a combination of sequences, whereby a first sequence, referred to as sequence 1, comprises a pulse train, whereas a following sequence, referred to as sequence 2, is a single pulse. Only after sequence 1 an echo is expected. By alternating sequence 1 and sequence 2 whereby sequence 1 has a phase shift $\pi$ compared to the sequence 2, and averaging the data, the result obtained indicates the effect of the pulse train applied in the sequence 1. The trigger for sampling is for each sequence provided at the same moment with regard to the end of the sequence. FIG. 10 illustrates the applied combination of sequences, wherein the moments of trigger are indicated. FIG. 11a to FIG. 11c illustrates the resulting EPR response obtained. FIG. 11a illustrates the background measurement, used for correcting and/or taking into account when evaluating the different measurements, FIG. 11b illustrates the EPR response using resovist, indicating an extension of the reply with 100 ns. FIG. 11c illustrates the EPR response using 25 nm superparamagnetic particles, resulting in an extension of the reply with 200 ns. Each of the drawings shows three curves, the full line corresponding with a static magnet field of 50 Gauss, the dashed line corresponding with a static magnet field of 90 Gauss and the dotted line corresponding with a static magnet field of 1500 Gauss. Furthermore an additional effect is seen after the pulse for these 25 nm particles. The effect is less pronounced for higher static magnetic fields.

Certain embodiments relate to computer-implemented methods for performing pulsed EPR or designing pulsed EPR experiments as indicated above or as can be obtained by the functionality of the system described above. Certain embodiments also relate to corresponding computing program products or a controller for controlling a system for performing pulsed EPR or designing pulsed EPR experiments as described above. Such methods may be implemented in a computing system, such as for example a general purpose computer. The computing system may comprise an input unit and a data processor, which may be set up as a single data processor or as a plurality of processors. The computing system may include a processor, a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of the standard processes of the method as set out above and optionally of the optional processes as set out above. Therefore, a computing system including instructions for implementing the method for performing or designing pulsed EPR is not part of the prior art.

Certain embodiments encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of performing pulsed electron paramagnetic resonance (EPR), the method comprising:
    generating a static magnetic field for applying to an object comprising probes with spins for providing an initial alignment of the spins;
    generating an excitation magnetic pulse train for applying to the object comprising probes with spins, the excitation magnetic pulse train comprising excitation magnetic pulses having a substantially different orientation than the static magnetic field; and
    detecting from the probes with spins an echo response induced by the excitation magnetic pulse train,
    wherein the probes with spins are broadband probes and wherein generating an excitation magnetic pulse train comprises selectively exciting predetermined frequencies of the probes, and wherein detecting comprises detecting an echo response without applying a rephrasing pulse.

2. The method according to claim 1, wherein generating an excitation pulse comprises generating an excitation pulse inducing positive interference effects between responses of the probes for forming the echo response.

3. The method according to claim 1, wherein detecting the echo response comprises topologically imaging echo responses from probes distributed in the object.

4. The method according to claim 1, wherein exciting predetermined frequencies of broadband probes of interest comprises exciting a limited number of frequencies of the wideband resonance of the probes.

5. The method according to claim 1, wherein detecting the echo response comprises detecting the echo response from single domain particles.

6. The method according to claim 5, wherein detecting the echo response comprises detecting the echo response from wideband resonance super paramagnetic particles.

7. The method according to claim 1, wherein generating an excitation pulse train comprises
    generating a sequence of EPR pulses wherein the shape of different EPR pulses in the sequence of EPR pulses is adapted for compensating at least partly for frequency dependency of the resonance of the spins of the probes in the object.

8. The method according to claim 1, wherein generating an excitation pulse train comprises generating a sequence of EPR pulses, wherein the intensity of different EPR frequencies in the sequence of EPR pulses is adapted for compensating at least partly for power dependency of the resonance of spin probes in the object or of a detection system.

9. A non-transitory computer-readable medium having stored therein a program which, when executed on a processor, performs the method according to claim 1.

10. A system for performing pulsed electron paramagnetic resonance (EPR), the system comprising:
    a static magnetic field generator configured to apply a static magnetic field to an object comprising probes with spins for providing an initial alignment of the spins;
    an excitation magnetic pulse train generator configured to generate an excitation magnetic pulse train comprising excitation magnetic pulses having a substantially different orientation than the static magnetic field for applying to the object comprising probes with spins; and
    a detection unit configured to detect from the probes with spins an echo response induced by the excitation magnetic pulse train,
    wherein the excitation magnetic pulse train generator comprises a controller configured to selectively excite predetermined frequencies of probes, and wherein the detection unit is configured to detect the echo response without applying a rephrasing pulse.

11. The system according to claim 10, wherein the controller is configured to generate with the excitation magnetic pulse train positive interference effects between responses of probes for forming the echo response.

12. The system according to claim 10, wherein the detection unit is configured to topologically image echo responses from probes distributed in the object.

13. The system according to claim 10, wherein the probes with spins are broadband probes.

14. The system according to claim 10, wherein the excitation magnetic pulse train generator is configured to excite a limited number of frequencies of the wideband resonance of the probes.

15. The system according to claim 10, wherein the detection unit is configured to detect the echo response from single domain particles.

16. The system according to claim 15, wherein the detection unit is configured to detect the echo response from wideband resonance super paramagnetic particles.

17. The system according to claim 10, wherein the static magnetic field generator is configured to generate a sequence of EPR pulses wherein the shape of different EPR pulses in the sequence of EPR pulses is adapted for compensating at least partly for frequency dependency of the resonance of the spins of the probes in the object.

18. The system according to claim 10, wherein the excitation magnetic pulse train generator is configured to generate a sequence of EPR pulses, wherein the intensity of different EPR frequencies in the sequence of EPR pulses is adapted for compensating at least partly for power dependency of the resonance of spin probes in the object or of a detection system.

19. A system for performing pulsed electron paramagnetic resonance (EPR), the system comprising:
    means for generating a static magnetic field for applying to an object comprising broadband probes with spins for providing an initial alignment of the spins;
    means for generating an excitation magnetic pulse train for applying to the object comprising probes with spins, the excitation magnetic pulse train comprising excitation magnetic pulses having a substantially different orientation than the static magnetic field; and
    means for detecting from the probes with spins an echo response induced by the excitation magnetic pulse train, wherein means for generating an excitation magnetic pulse train comprises means for selectively exciting predetermined frequencies of the probes, and wherein means for detecting an echo response comprises means for detecting an echo response without applying a rephasing pulse.

* * * * *

UNITED STATES PATENT AND TRADEMARK OFFICE
CERTIFICATE OF CORRECTION

| | | |
|---|---|---|
| PATENT NO. | : 8,816,685 B2 | Page 1 of 1 |
| APPLICATION NO. | : 13/075087 | |
| DATED | : August 26, 2014 | |
| INVENTOR(S) | : Vaes et al. | |

It is certified that error appears in the above-identified patent and that said Letters Patent is hereby corrected as shown below:

In the Specification

In column 5 at line 14, change "consists of" to --consists of,--.

In the Claims

In column 11 at lines 59-60, in Claim 1, change "rephrasing" to --rephasing--.

In column 12 at line 44, in Claim 10, change "rephrasing" to --rephasing--.

Signed and Sealed this
Thirty-first Day of March, 2015

Michelle K. Lee
*Director of the United States Patent and Trademark Office*